US008039513B2

(12) United States Patent
Kang et al.

(10) Patent No.: US 8,039,513 B2
(45) Date of Patent: Oct. 18, 2011

(54) CIS-1,2-SUBSTITUTED STILBENE DERIVATIVES AND THEIR USE IN PREPARATION OF DRUGS FOR TREATMENT AND/OR PREVENTION OF DIABETES

(75) Inventors: Zhiyun Kang, Beijing (CN); Zuze Wu, Beijing (CN); Zhuangrong Sun, Beijing (CN); Zhongxiong Tang, Beijing (CN)

(73) Assignee: Institute of Radiation Medicine, Academy of Military Medical Sciences, PLA, Beijing (CN)

( * ) Notice: Subject to any disclaimer, the term of this patent is extended or adjusted under 35 U.S.C. 154(b) by 443 days.

(21) Appl. No.: 11/658,239

(22) PCT Filed: Jul. 20, 2005

(86) PCT No.: PCT/CN2005/001086
§ 371 (c)(1),
(2), (4) Date: Nov. 24, 2008

(87) PCT Pub. No.: WO2006/007794
PCT Pub. Date: Jan. 26, 2006

(65) Prior Publication Data
US 2009/0076114 A1 Mar. 19, 2009

(30) Foreign Application Priority Data

Jul. 21, 2004 (CN) .......................... 2004 1 0069374

(51) Int. Cl.
*A01N 33/00* (2006.01)
*A01N 37/18* (2006.01)
*A61K 31/13* (2006.01)
*A61K 31/16* (2006.01)
*A61K 31/165* (2006.01)
*C07C 43/02* (2006.01)
*C07C 233/00* (2006.01)
*C07C 235/00* (2006.01)
*C07C 237/00* (2006.01)

(52) U.S. Cl. ........ 514/579; 514/613; 514/617; 514/622; 514/720; 568/646; 564/161; 564/169; 564/180

(58) Field of Classification Search .................. None
See application file for complete search history.

(56) References Cited

U.S. PATENT DOCUMENTS

| 4,996,237 | A * | 2/1991 | Pettit et al. ................. 514/720 |
| 5,525,632 | A | 6/1996 | Obsumi et al. ............... 514/646 |
| 5,731,353 | A | 3/1998 | Ohsumi et al. |
| 6,245,814 | B1 * | 6/2001 | Nag et al. .................... 514/570 |

FOREIGN PATENT DOCUMENTS

| CN | 1294912 | 5/2001 |
| JP | 7-228558 | 8/1995 |
| JP | 9-59245 | 3/1997 |
| JP | 2002-537250 | 11/2002 |
| JP | 2003-507356 | 2/2003 |
| JP | 2003-521500 | 7/2003 |
| JP | 2004-537561 | 12/2004 |
| JP | 2005-507912 | 3/2005 |
| WO | 9956737 A1 | 11/1999 |
| WO | 0048590 A1 | 8/2000 |
| WO | WO00/69430 * | 11/2000 |
| WO | 01/12579 | 2/2001 |
| WO | 01/56382 | 8/2001 |
| WO | 0249994 A2 | 6/2002 |
| WO | 0250007 A2 | 6/2002 |
| WO | 03/009838 | 2/2003 |
| WO | 03035008 A2 | 5/2003 |

OTHER PUBLICATIONS

Byrn et al. Solid-State Chemistry of Drugs, 2d, Chapter 11 Hydrates and Solvates, 233-247, 1999.*
Morissette et al. Adv. Drug Delivery Rev. 2004, 56, 275-300.*
Alexander et al., "Preparation of Some Substituted α,β-Diphenylacrylic Acids and Related Derivatives" The Journal of Organic Chemistry 23: 389-391, Mar. 1958.
Cushman et al., "Synthesis and Evaluation of Stilbene and Dihydrostilbene Derivatives as Potential Anticancer Agents That Inhibit Tubulin Polymerization" J. Med. Chem. 34: 2579-2588, 1991.
Cushman et al., "Synthesis and Evaluation of Analogues of (Z)-1-(4-Methoxyphenyl)-2-(3,4,5-trimethoxyphenyl)ethene as Potential Cytotoxic and Antimitotic Agents" J. Med. Chem. 35: 2293-2306, 1992.
Kamoda et al., "A Common Structure of Substrate Shared by Lignostilbenedioxygenase Isozymes from *Sphingomonas paucimobilis* TMY1009" Biosci. Biotechnol. Biochem. 67(6): 1394-1396, 2003.
Kuo et al., "Synthesis, Structure-Activity Relationships, and Pharmacokinetic Properties of Dihydroorotate Dehydrogenase Inhibitors: 2-Cyano-3-cyclopropyl-3-hydroxy-N-[3'-methyl-4'-(trifluoromethyl)phenyl]propenamide and Related Compounds" J. Med. Chem. 39: 4608-4621, 1996.
Noyce et al., "The Kinetics and Mechanism of the Acid-Catalyzed Isomerization of cis-Stilbene" Journal of the American Chemical Society 90(17): 4633-4637, Aug. 14, 1968.
Pinney et al., "Synthesis and Biological Evaluation of Aryl Azide Derivatives of Combretastatin A-4 as Molecular Probes for Tubulin" Bioorganic & Medicinal Chemistry 8: 2417-2425, 2000.
Solladie et al., "A re-investigation of resveratrol synthesis by Perkins reaction. Application to the synthesis of aryl cinnamic acids" Tetrahedron 59: 3315-3321, 2003.
European Search Report, mailed Aug. 19, 2009, for PCT/CN2005/001086, 11 pages.
Gankroger et al., "Structural requirements for the interaction of combretastatins with tubulin: how important is the trimethoxy unit?," Org. Biomol. Chem. 1:3033-3037, 2003.
Michel et al., "The Effect of Various Acrylonitriles and Related Compounds on Prostaglandin Biosynthesis," *Prostaglandins* 27(1):69-84, 1984.

* cited by examiner

*Primary Examiner* — Traviss C McIntosh, III
(74) *Attorney, Agent, or Firm* — Seed IP Law Group PLLC

(57) ABSTRACT

The present invention relates to cis-1,2-substituted stilbene derivatives, or their pharmaceutically acceptable salts, glucosides or solvates, a pharmaceutical composition comprising the compound, and use of said compound for preparation of a drug for treatment and/or prevention of diabetes or improvement of diabetic complications.

5 Claims, No Drawings

CIS-1,2-SUBSTITUTED STILBENE DERIVATIVES AND THEIR USE IN PREPARATION OF DRUGS FOR TREATMENT AND/OR PREVENTION OF DIABETES

TECHNICAL FIELD

This invention relates to the use of cis-1,2-substituted stilbene derivatives or their pharmaceutically acceptable salts, glucosides or solvates in preparation of drugs for treatment and/or prevention of diabetes or alleviation of diabetic complications.

BACKGROUND ART

Diabetes is a clinically familiar chronic metabolic disease all over the world. In recent years, the world-wide morbidity rate of diabetes is rising rapidly along with the economic development and changes in dietary structure. According to statistics, the total number of diabetic patients can be 120 millions, among which more than 30 millions are Chinese. Most of the patients are insulin-independent, i.e., type II diabetes. At present, diabetes has become the third severe disease threatening the health of humans following cardiovascular disease and cancer. The duration of illness for diabetes is long and its complications occur usually during inadequate treatment, such as chronic vascular complications (including cerebrovascular disorders, ischemic heart disease), diabetic nephropathy, and so on. The mortality due to diabetes and its complications is also elevating year after year. Therefore, treatment and prevention of diabetes and its complications have become a key research task confronting medical and pharmaceutical workers of the world.

At present, the clinically used oral hypoglycemic agents are mainly Western drugs, which can be classified by their chemical structures as: sulfonylureas, biguanides, phenylalanines, thiazolidyldiketones, and glycolipids. Besides, there are 1,2-stilbene compounds which are now in research and development. According to the reports of U.S. Pat. No. 6,410,596 and CN1398838A, 1,2-stilbene compounds are present in many kinds of plants. Up to now, at least several decades of plants of 31 genues in 21 families are found to contain these compounds. At the meantime, these compounds are found to have extensive physiologic functions, such as anti-oxidation, anti-tumor, anti-blood stasis syndrome, hypoglycemic effect, and so forth. However, the 1,2-stilbenes having the above-mentioned functions are all trans-1,2-substituted stilbene derivatives. Concerning the activity of cis-1,2-substituted stilbene derivatives, only U.S. Pat. No. 5,525,632 reported that combrotastatin and its derivatives possessed anti-tumor function.

CONTENT OF THE INVENTION

The present inventors discovered that cis-1,2-substituted stilbene compounds, their pharmaceutically acceptable salts, glucosides or solvates all had good hypoglycemic and other functions. Therefore, they can be used in treatment and/or prevention of diabetes and improvement of diabetic complications.

The first aspect of this invention relates to cis-1,2-substituted stilbene compounds of formula I, their pharmaceutically acceptable salts, glucosides or solvates:

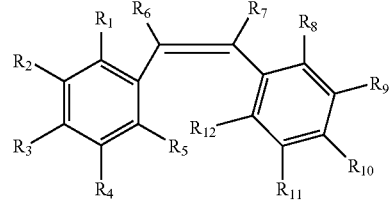

in which, $R_1$-$R_{12}$, which may be same or different, each independently represent hydrogen; hydroxyl group; $C_1$-$C_6$ alkyl group; $C_1$-$C_6$ alkoxyl group; $C_1$-$C_6$ ester group; amino group; $C_1$-$C_6$ alkylamino group; $C_1$-$C_6$ alkyl sulfonyl group, sulfamido, sulfonylurea group, guanidino group, carboxyl group, amido group; $C_1$-$C_6$ acyl group, nitro group, cyano group, halogen, $OM_1$, $M_2$, or $SO_2OM_3$ group, wherein $M_1$, $M_2$ and $M_3$, which may be same or different, each independently represent hydrogen or a cation chosen from alkali or alkaline earth metals, $NH_4^+$, or a sugar-containing glycoside.

The second aspect of this invention relates to a pharmaceutical composition comprising, as active ingredient, the cis-1,2-substituted stilbene compounds of formula I, their pharmaceutically acceptable salts, glucosides or solvates as well as one or more pharmaceutically acceptable vehicles or excipients.

The third aspect of this invention relates to use of the cis-1,2-substituted stilbene compounds of formula I, their pharmaceutically acceptable salts, glucosides or solvates for preparation of drugs for treatment and/or prevention of diabetes or improvement of diabetic complications,

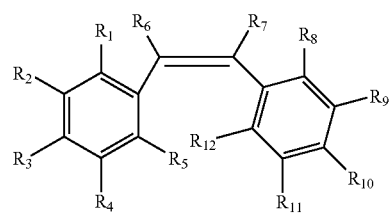

in which, $R_1$-$R_{12}$, which may be same or different, each independently represent hydrogen, hydroxyl group; $C_1$-$C_6$ alkyl group, $C_1$-$C_6$ alkoxyl group; $C_1$-$C_6$ ester group, amino group; $C_1$-$C_6$ alkylamino group; $C_1$-$C_6$ alkyl sulfonyl group, sulfamido, sulfonylurea group, guanidino group, carboxyl group, amido group; $C_1$-$C_6$ acyl group, nitro group, cyano group, halogen, $OM_1$, $M_2$, or $SO_2OM_3$ group, wherein $M_1$, $M_2$ and $M_3$, which may be same or different, each Independently represent hydrogen or a cation chosen from alkali or alkaline earth metals, $NH_4^+$, or a sugar-containing glycoside.

The fourth aspect of this invention relates to a method for treatment and/or prevention of diabetes and improvement of diabetic complications, which comprises administering an effective amount of the compounds of Formula I to the patients in need thereof.

In a preferred embodiment of this invention, the compounds of Formula I have the following structures represented by Formula II, Formula III and Formula IV:

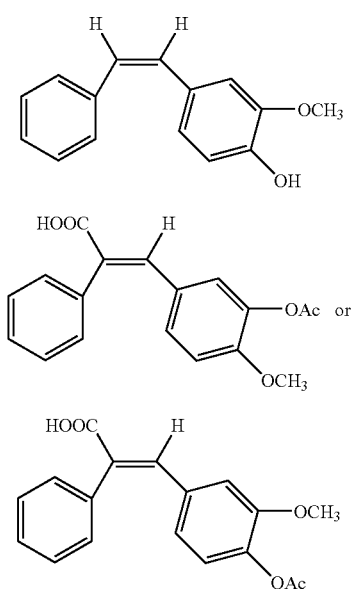

In another preferred embodiment of this invention, the compounds of Formula I have the following structure represented by Formula V:

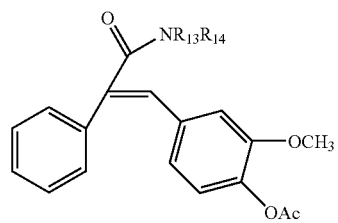

in which, $R_{13}$, $R_{14}$, which may be same or different, each independently represent hydrogen; $C_1$-$C_7$ alkyl group; $C_1$-$C_6$ alkoxyl group; $C_1$-$C_6$ ester group, amino group; $C_1$-$C_6$ alkylamino group, $C_1$-$C_6$ alkyl sulfonyl group, sulfamido group, sulfonylurea group, guanidino group.

In a further preferred embodiment of this invention, the glycoside is glucoside or mannoside, or the solvate is hydrate.

The compound of Formula I in this invention is prepared from substituted phenylacetic acid and substituted benzaldehyde via Perkin reaction.

The term "pharmaceutically acceptable salts" used herein refers to the salts formed with pharmaceutically usable inorganic acids, such as sulfate, hydrochloride, hydrobromate, phosphate, or the salts formed with pharmaceutically usable organic acids, such as acetate, oxalate, citrate, gluconate, succinate, tartrate, p-toluene sulfonate, methylsulfonate, benzoate, acetate, maleate, etc.

The present compounds can be utilized alone or in the form of pharmaceutical composition, which, according to different administration routes, can be made into intestinally or parenterally administered preparations, such as tablets, capsules, granules, injections, suppositories, drops, or patches, etc.

The above-mentioned administration routes include oral administration, spray inhalation, nasal administration, buccal absorption, local application, and parenteral (subcutaneous, intravenous, or intramuscular) ad ministration, preferably oral or intravenous administration.

When administered orally, the compound of the invention may be produced in any orally acceptable formulation forms comprising, but being not limited to, tablets, capsules, aqueous solutions or aqueous suspensions. Typically, the vehicles used for tablets include lactose and corn starch. In addition, lubricating agents such as magnesium stearate may also be added. Usually, diluents used for capsules include lactose and dried corn starch. Aqueous suspension formulations generally include mixture of the active ingredient with suitable emulsifying and suspending agents. Optionally, the oral formulation forms may further comprise sweetening agents, flavoring agents or coloring agents.

For local application, the compounds can be formulated into a suitable ointment, lotion or cream, wherein the active ingredient suspends or dissolves in one or more vehicles. The vehicles suitable for ointment include, but are not limited to, mineral oil, liquid petrolatum, white petrolatum, propylene glycol, polyoxyethylene, polyoxypropylene, emulsifying wax and water; and the vehicles suitable for lotion or cream include, but are not limited to, mineral oil, sorbitan monostearate, Tween 60, cetyl ester wax, cetearyl alcohol, 2-octyldodecanol, benzyl alcohol and water.

The compounds of the present invention may be administered in the form of sterile injection preparations, for example, as sterile injection aqueous or oleaginous suspensions or sterile injection solutions. The acceptable vehicles and solvents include water, Ringer's solution and isotonic sodium chloride solution. In addition, sterile, fixed oils, such as mono- or diglycerides, can be also employed as solvents or suspending mediums.

In addition, the dosage level and usage method of the present compound depend upon a variety of factors including, the age, body weight, gender, natural health condition, and nutritional status of the subject, the time of administration, the rate of metabolism, the severity of the particular disease being treated, and the subjective judgment of the doctor for diagnosis. The dosage levels on the order of about 0.01 mg to about 100 mg of the active ingredient/kg body weight/day are preferred.

MODE OF CARRYING OUT THE INVENTION

The following examples are detailed further explanations for this invention, but do not intend to limit the present invention.

Example 1

Preparation of cis-1-phenzyl-2-(3'-methoxy-4'-hydroxy-phenyl)ethene (Compound of Formula II)

1.5 g α-3-methoxy-4-hydroxy-phenyl cinnamic acid was weighted and put into a 100 ml three-necked bottle with reflux tube and magnetic stirrer. Then, 7 ml quinoline, 0.25 g copper powder were added. The mixture was heated at 210° C. using an electric heater with stirring for one hour. Carbon dioxide gas was released during the reaction along with slight explosive sound. After completion of the reaction, 20 ml ethyl acetate was added when the system was slightly cooled down. After filtration, the reaction solution was washed with 2N HCL, and then with water, followed by dehydrating with anhydrous $MgSO_4$. After decarboxylation, the resultant stilbene had very strong fluoroscence, whereas the α-3-methoxy-4-hydroxy-phenyl cinnamic acid did not. By column chromatography (chloroform:methanol=9.5:0.5), a yellow solid was obtained. MS (FAB) m/Z: M⁺ 226.0. ¹H NMR (deuterated DMSO) δ9.16 (s 1H —OH), 3.84 (s 3H —OCH₃), 7.54 (d 2H 2,6-H), 6.78 (d 1H 2-H), 7.37 (t 2H α,β-H), 7.35, 7.26, 7.69 (arom 5H).

Example 2

Preparation of cis-2-phenyl-3-(3'-acetoxy-4'-methoxy-phenyl)acrylic acid (Compound of Formula III)

13.6 g (0.1 mole) phenylacetic acid, 15.2 g (0.1 mole) isovanillin, 12 ml (0.07 mole) triethylamine, and 18 ml (0.18 mole) acetic anhydride were put into a 250 ml three-necked bottle. The mixture was refluxed in an oil bath at 110° C. with magnetic stirring for 12 hours. After completion of the reaction, the system was cooled down to room temperature, to which 200 ml ethyl acetate was added. Then, the reaction solution was washed with water till neutral pH and dehydrated with anhydrous Na₂SO₄ overnight. After removing the desiccant, the solvent was eliminated under reduced pressure. Thereafter, anhydrous ethyl ether was added to separate out 7.55 g of a white solid, with mp of 180-190° C. and yield of 27.9%.

The compound with molecular formula $C_{18}H_{16}O_5$ had molecular weight of 312.31; MS (FAB) m/Z M⁺ 312.0, ¹HNMR (deuterated) δ8.81 (s 1H, —OH), 3.07 (s 3H, —OCH₃), 2.73 (s 3H, CH₃), 7.40, 7.39, 7.18, 6.95 (2-H), 6.72 (s 1H, β-H), 3.72 (s 3H, —OCH₃), 7.40, 7.39, 7.18, 6.95 (arom 7H).

Example 3

Preparation of cis-2-phenyl-3-(3'-methoxy-4'-acetoxy-phenyl)acrylic acid (Compound of Formula IV)

13.6 g (0.1 mole) phenylacetic acid, 15.2 g (0.1 mole) vanillin, 12 ml (0.07 mole) triethylamine, 18 ml (0.18 mole) acetic anhydride were put into a 250 ml three-necked bottle. The mixture was refluxed in an oil bath at 110° C. with magnetic stirring for 12 hours. After completion of the reaction, the system was cooled down to room temperature, to which 200 ml ethyl acetate was added. Then, the reaction solution was washed with water till neutral pH and dehydrated with anhydrous Na₂SO₄ overnight. After removing the desiccant, the solvent was eliminated under reduced pressure. Thereafter, anhydrous ethyl ether was added to separate out 1.11 g of a white solid, with mp of 200-210° C. and yield of 40%.

The compound with molecular formula $C_{18}H_{16}O_5$ had molecular weight of 312.31, MS (FAB) m/Z M+313.

Elementary analysis: molecular formula $C_{18}H_{16}O_5$; molecular weight 312.31.

| Theoretic value | C 69.22% | H 5.13% |
| Analytic value | C 69.32% | H 5.13%. |

Example 4

Preparation of cis-2-phenyl-3-(3'-methoxy-4'-hydroxy-phenyl)acrylic acid 100 ml anhydrous methanol and 0.5 g metallic sodium were put into a 250 ml three-necked bottle and stirred till complete dissolution of sodium. Then, 9.4 g of the compound prepared in Example 3 was added, followed by stirring at room temperature for 5 hours and heating in a water bath at 50° C. for one hour. Thereafter, the reaction solution was adjusted to be acidic with 15% HCl, followed by removing the solvent under reduced pressure to get a solid. The solid was washed with water, and recrystallized with 30% ethanol to obtain 7.94 g of a white crystalline solid, with mp of 198-202° C. and yield of 91%.

Elementary analysis: molecular formula $C_{16}H_{14}O_4$: molecular weight 270.28.

| Theoretic value | C 71.11% | H 5.19% |
| Analytical value | C 70.92% | H 5.10%. |

Example 5

Preparation of cis-2-phenyl-3-(3'-carboxy-4'-methoxy-phenyl)acrylic acid 100 ml anhydrous methanol and 0.5 g metallic sodium were put into a 250 ml three-necked bottle and stirred till complete dissolution of sodium. 3.2 g of the compound prepared in Example 2 was added, followed by stirring at room temperature for 3 hours and heating in a water bath at 50° C. for one hour. Thereafter, the reaction solution was adjusted to be acidic with 15% HCl, followed by removing the solvent under reduced pressure to get a solid. The solid was washed with water, and recrystallized with 95% ethanol to obtain 2.3 g of a white crystalline solid, with mp of 220-224° C. and yield of 85.2%.

Elementary analysis: molecular formula $C_{15}H_{14}O_4$; molecular weight 270.28

| Theoretic value | C 71.11% | H 5.19% |
| Analytic value | C 71.24% | H 5.18%. |

Example 6

Preparation of cis-2-phenyl-3-(3-methoxy-4'-acetoxy-phenyl)-N-cyclohexyl acrylamide 9.36 g (0.03 mole) cis-2-phenyl-3-(3-methoxy-4-acetoxy-phenyl)acrylic acid was put into a 100 ml three-necked bottle. Then, 22 ml (0.3 mole) thionyl chloride and 50 ml anhydrous toluene were added, followed by refluxing at 100-110° C. with heating and stirring for 3 hours. After completion of the reaction, surplus thionyl chloride was removed by suctioning to dryness under reduced pressure. A suitable amount of toluene was added and suctioned to dryness under reduced pressure (repeating for two times) to obtain a red sticky liquid. Then, 30 ml anhydrous toluene was added to the obtained liquid, followed by stirring and dropping 6 ml (0.05 mole) cyclohexylamine at room temperature. After completion of the dropping, the reaction was carried out at 50° C. with stirring for 3 hours, and then toluene was removed under reduced pressure to get a red oily substance. Thereafter, ethyl acetate was added to the obtained oily substance with stirring to precipitate a solid. The solid was collected by filtration and then washed with ethyl acetate for three times to obtain 3.6 g of a product with mp of 124-127° C. and yield of 30%.

Elementary analysis: molecular formula $C_{24}H_{27}O_4$, molecular weight 393.48

| Theoretic value | C 73.26% | H 6.92% | N 3.56% |
|---|---|---|---|
| Analytical value | C 73.37% | H 6.91% | N 3.54%. |

Example 7

Preparation of cis-2-phenyl-3-(3'-methoxy-4'-acetoxy-phenyl)-N-(methylene furan)acrylamide 6.24 g (0.02 mole) cis-2-phenyl-3-(3'-methoxy-4'-acetoxy-phenyl)-acrylic acid and 20 ml (0.28 mole) thionyl chloride were put into a 50 ml three-necked bottle, before stirring and refluxing by heating for 3 hours. Thereafter, surplus thionyl chloride was removed by suctioning to dryness under reduced pressure. Ethyl ether was added, followed by dropping 6 g of 2-aminomethyl-tetrahydrofuran with stirring. After completion of the dropping, the system was continuously stirred at room temperature for one hour to precipitate a solid. The solid was collected by filtration and recrystallized with methanol-ethyl ether, to obtain 6.4 g of a refined product with mp of 119-121° C. and yield of 80%.

Elementary analysis: molecular formula $C_{23}H_{25}NO_5$; molecular weight 395.45

| Theoretic value | C 69.85% | H 6.37% | N 3.54% |
|---|---|---|---|
| Analytical value | C 69.55% | H 6.32% | N 3.25%. |

Example 8

Preparation of cis-2-phenyl-3-(3'-methoxy-4'-acetoxy-phenyl)-N-(4-methylcyclohexyl)acrylamide According to the method stated in Example 7, cis-2-phenyl-3-(3'-methoxy-4'-acetoxy-phenyl)-N-(4-methylcyclohexyl)acrylamide was prepared with mp of 136-140° C.

Elementary analysis: molecular formula $C_{25}H_{29}NO_4$; molecular weight 407.51

| Theoretic value | C 73.69% | H 7.17% | N 3.44% |
|---|---|---|---|
| Analytical value | C 73.64% | H 7.29% | N 3.61%. |

Example 9

Preparation of cis-2-phenyl-3-(3',4'-dimethoxy-phenyl)-methyl acrylate 5.4 g cis-2-phenyl-3-(3'-methoxy-4'-hydroxy-phenyl) acrylic acid, 10 g dimethyl sulfate, and 40 ml methylene chloride were put into a 50 ml three-necked bottle, to which 40 ml 10% sodium hydroxide solution was dropped with stirring at 40° C. After completion of the dropping, the reaction was continued for 4 hours, followed by standing to separate out the organic phase. Then, the organic phase was washed with water and dried with anhydrous sodium sulfate. After removing the desiccant by filtration, the filtrate was concentrated to eliminate methylene chloride, to get a white solid. The solid was then recrystallized with methanol, to obtain 2.5 g of a refined product with mp of 100-103° C. and yield of 78%.

Elementary analysis: molecular formula $C_{18}H_{18}O_4$; molecular weight 298.34

| Theoretic value | C 72.47% | H 6.08% |
|---|---|---|
| Analytic value | C 72.13% | H 6.04%. |

Example 10

Preparation of cis-2-phenyl-3-(3'-methoxy-4'-acetoxy-phenyl)pyrrolidinyl acrylamide According to the method stated in Example 7, cis 2-phenyl-3-(3'-methoxy-4'-acetoxy-phenyl)pyrrolidinyl acrylamide (N365) was prepared with mp of 113-116° C.

Elementary analysis: molecular formula $C_{22}H_{33}NO_4$, molecular weight 365.472

| Theoretic value | C 72.296% | H 6.34% | N 3.85% |
|---|---|---|---|
| Analytic value | C 72.475% | H 6.41% | N 4.08%. |

Example 11

Biological Activity

In the following biological experiments, the hypoglycemic activity of the above compounds was chiefly observed in hyperglycemic mice. Taking 3,3',5'-trihydroxy-4'-methoxystilbene-3-O-β-D-glucoside (rhaponticin) as a positive control drug, the hypoglycemic activity of these compounds were preliminarily evaluated.

Kun Ming male mice (certification: Medical Animal No. D01-3023) with body weight of 21-33 g were used in the experiments. After fasting and feeding water for 16 hours, the compounds were administered to the mice. The candidate compounds were formulated with dimethyl sulfoxide (2.5 ml/kg), and administered to the mice intragastrically. After fifteen minutes, glucose (2 g/10 ml/kg) was administered orally. One hour later, one drop of blood was collected by cutting a segment of tail and the blood sugar level was monitored with a blood sugar monitor manufactured by Johnson Company, USA, by using a test paper containing glucose oxidase. For the mice of the control group, dimethyl sulfoxide (205 ml/kg) and glucose (2 g/10 ml/kg) were given intragastrically. The results were listed in Table 1-3:

TABLE 1

Hypoglycemic effect of orally administered compounds stated in Examples 1, 2 and 3 in mice with glucose-induced hyperglycemia

| Compound | Dosage (mg/kg) | Number of mice | Blood sugar level one hour after administration M ± SD (mmol/L) |
|---|---|---|---|
| DMSO | 400 | 5 | 9.50 ± 1.06 |
| rhaponticin | 400 | 5 | 9.14 ± 1.90 |
|  | 800 | 5 | 7.02 ± 1.01 |
| Example 1 | 400 | 5 | 7.62 ± 1.59 |
| Example 2 | 400 | 5 | 8.20 ± 0.99 |
| Example 3 | 400 | 5 | 7.30 ± 0.68 |

TABLE 2

Hypoglycemic effect of orally administered compounds stated in
Examples 4, 5 and 6 in mice with glucose-induced hyperglycemia

| Compound | Dosage (mg/kg) | Number of mice | Blood sugar level one hour after administration M ± SD (mmol/L) |
|---|---|---|---|
| DMSO | | 10 | 8.53 ± 0.76 |
| Example 3 | 400 | 6 | 7.85 ± 0.16 |
| Example 4 | 400 | 6 | 7.30 ± 2.21 |
| Example 5 | 400 | 6 | 8.50 ± 1.01 |
| Example 6 | 400 | 6 | 5.46 ± 0.86 |

TABLE 3

Hypoglycemic effect of orally administered compounds stated in
examples 7, 8 and 9 in mice with glucose-induced hyperglycemia

| Compound | Dosage (mg/kg) | Number of mice | Blood sugar level one hour after administration M ± SD (mmol/L) |
|---|---|---|---|
| DMSO | | 6 | 7.80 ± 1.33 |
| Example 7 | 400 | 6 | 6.95 ± 0.61 |
| Example 8 | 100 | 6 | 5.61 ± 1.67 |
| Example 9 | 400 | 6 | 8.41 ± 0.88 |

The invention claimed is:

1. A compound having the following structure (V):

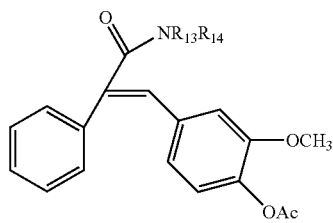

wherein, $R_{13}$ and $R_{14}$ are each independently hydrogen, a $C_1$-$C_7$ alkyl group, a $C_1$-$C_6$ alkoxyl group, a $C_1$-$C_6$ ester group, an amino group, a $C_1$-$C_6$ alkylamino group, a $C_1$-$C_6$ alkyl sulfonyl group, a sulfamido group, a sulfonylurea group, a guanidino group, or a pharmaceutically acceptable salt thereof.

2. A pharmaceutical composition comprising the compound according to claim 1 or a pharmaceutically acceptable salt thereof and one or more pharmaceutically acceptable vehicles or excipients.

3. The pharmaceutical composition according to claim 2, wherein the pharmaceutical composition is in the form of tablets, capsules, granules, patches, suppositories, drops or injections.

4. A method for treatment of diabetes and improvement of diabetic complications the method comprising administering an effective amount of the compound according to claim 1, or a pharmaceutically acceptable salt thereof, to a patient suffering from diabetes.

5. A compound, wherein the compound has one of the following structures:

or a pharmaceutically acceptable salt thereof.

* * * * *